(12) United States Patent
Park et al.

(10) Patent No.: US 9,180,082 B2
(45) Date of Patent: Nov. 10, 2015

(54) BIOTIN-CONJUGATED HEXAPEPTIDE-2 DERIVATIVE AND USE THEREOF

(71) Applicant: INCOSPHARM CORPORATION, Daejeon (KR)

(72) Inventors: Kee-Don Park, Daejeon (KR); Chae-Jin Lim, Daejeon (KR); Seok-Jeong Yoon, Daejeon (KR); Seon-Deok Kwon, Daejeon (KR)

(73) Assignee: INCOSPHARM CORPORATION, Daejeon (KR)

(*) Notice: Subject to any disclaimer, the term of this patent is extended or adjusted under 35 U.S.C. 154(b) by 0 days.

(21) Appl. No.: 14/388,771

(22) PCT Filed: Mar. 27, 2013

(86) PCT No.: PCT/KR2013/002554
§ 371 (c)(1),
(2) Date: Sep. 26, 2014

(87) PCT Pub. No.: WO2013/147512
PCT Pub. Date: Oct. 3, 2013

(65) Prior Publication Data
US 2015/0057230 A1     Feb. 26, 2015

(30) Foreign Application Priority Data

Mar. 28, 2012 (KR) ........................ 10-2012-0031853

(51) Int. Cl.
*A61K 8/64*     (2006.01)
*A61K 38/08*     (2006.01)
*A61Q 19/08*     (2006.01)
*C07K 7/06*     (2006.01)

(52) U.S. Cl.
CPC . *A61K 8/64* (2013.01); *A61K 38/08* (2013.01); *A61Q 19/08* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 6,525,047 B2 | 2/2003 | Carpino et al. |
| RE38,524 E | 6/2004 | Carpino et al. |
| 6,924,280 B2 | 8/2005 | Carpino et al. |
| 6,951,850 B2 | 10/2005 | Carpino et al. |
| 6,953,791 B2 | 10/2005 | Carpino et al. |
| 7,989,590 B2 | 8/2011 | Honma et al. |
| 8,722,626 B2 | 5/2014 | Acosta et al. |

(Continued)

FOREIGN PATENT DOCUMENTS

| | | |
|---|---|---|
| EP | 1001970 B1 | 5/2000 |
| EP | 1713433 B1 | 10/2006 |

(Continued)

OTHER PUBLICATIONS

EESR in corresponding EP application No. 13718774.6, (2014).

*Primary Examiner* — Jeffrey E Russel
(74) *Attorney, Agent, or Firm* — McDermott Will & Emery LLP

(57) ABSTRACT

The present invention relates to a biotin-conjugated hexapeptide-2 derivative or a pharmaceutically acceptable salt thereof and use thereof. More particularly, the present invention relates to a biotin-conjugated hexapeptide-2 derivative or a pharmaceutically acceptable salt thereof, a preparation method thereof, a composition including the same as an active ingredient, and a method for improving wrinkles and inhibiting skin aging using the same.

4 Claims, 2 Drawing Sheets

(56) References Cited

U.S. PATENT DOCUMENTS

| | | |
|---|---|---|
| 2007/0134189 A1 | 6/2007 | Golz-Berner et al. |
| 2008/0076718 A1 | 3/2008 | Reboud-Ravaux et al. |
| 2009/0181888 A1 | 7/2009 | Murakami et al. |
| 2009/0221512 A1 | 9/2009 | Acosta et al. |

FOREIGN PATENT DOCUMENTS

| | | |
|---|---|---|
| EP | 1967208 A1 | 9/2008 |
| EP | 1994939 A1 | 11/2008 |
| KR | 10-2004-0021993 A | 3/2004 |
| KR | 10-2008-0075530 A | 8/2008 |
| KR | 10-2008-0100378 A | 11/2008 |
| WO | 20071068998 A1 | 6/2007 |

BIOTIN-CONJUGATED HEXAPEPTIDE-2 DERIVATIVE AND USE THEREOF

SEQUENCE LISTING

The instant application contains a Sequence Listing which has been submitted electronically in ASCII format and is hereby incorporated by reference in its entirety. Said ASCII copy, created on Jul. 27, 2015, is named "OPP20143069US-sequence listing.txt" and is 428 bytes in size.

TECHNICAL FIELD

The present invention relates to a biotin-conjugated hexapeptide-2 derivative or a pharmaceutically acceptable salt thereof and use thereof. More particularly, the present invention relates to a biotin-conjugated hexapeptide-2 derivative or a pharmaceutically acceptable salt thereof, a preparation method thereof, a composition including the same as an active ingredient, and a method for improving wrinkles and inhibiting skin aging using the same.

BACKGROUND ART

Skin is an organ carrying out functions such as protection, barrier, temperature controlling, excretion and respiration, and is composed of epidermis, dermis, and subcutaneous fat. Epidermis is the thinnest layer and is an organized construction of keratinocytes and melanocytes. Dermis is a layer that makes up approximately 95% of the skin and functions to moisturize and protect the skin. In the dermis, collagen and elastin that play an important role in skin elasticity (wrinkle) are distributed to form a net-like structure, blood vessels and nerves are found, and mast cells involved in allergic reaction and natural moisturizing factors such as Na-PCA or hyaluronic acid are also included. Subcutaneous fat functions to provide nutrients for the epidermis and dermis, determine the body shape, maintain body temperature, absorb external impacts, and protect cells under the subcutaneous fat.

The skin aging occurs with time because of rapid reduction of skin functions due to endogenous or exogenous factors. With skin aging, the epidermis, dermis, and subcutaneous fat that are components of the skin become thin, and collagen and elastin also become thin and loose and begin to lose their elasticity, causing wrinkles. Also, aging or UV exposure of skin inhibits adipogenesis in subcutaneous adipocytes, leading to loss of skin's protective function and rapid skin aging. Therefore, the tissues of face, breast and hip become droopy and wrinkle development occurs, eventually fail to have the beauty of appearance.

Many studies have been made to improve the reduced skin function, and the most important method is to find a method of promoting collagen biosynthesis of skin cells. To achieve this, vitamin C and derivatives thereof, KTTKS peptide (SEQ ID NO. 1), copper peptide and various natural extracts have been selected and used. However, vitamin C and derivatives thereof have disadvantages of a low stability and a low long-term activity, and KTTKS peptide (SEQ ID NO. 1) and copper peptide have a disadvantage of having a low collagen biosynthesis-promoting effect. The natural extracts have disadvantages of low activity and difference in their activity at the time of sample preparation. Accordingly, there is an urgent need to develop a new concept material for promoting collagen biosynthesis in order to solve all the disadvantages.

DISCLOSURE

Technical Problem

Therefore, the present inventors have examined the prior arts in order to solve the problems. As a result, they found that hexapeptide-2 (His-D-Trp-Ala-Trp-D-Phe-Lys-NH$_2$) is able to promote fibroblast growth (Korean Patent Publication No. 10-2008-0075530), and they performed an experiment to provide it with a new activity through various modifications and conjugations thereof. Finally, the present inventors demonstrated that a biotin-conjugated hexapeptide-2 peptide derivative has excellent ability to promote collagen production in fibroblasts, and the peptide derivative can be used for improving skin wrinkles and skin aging.

Technical Solution

An object of the present invention is to provide a novel peptide derivative or a pharmaceutically acceptable salt thereof having an excellent effect of promoting collagen biosynthesis in fibroblasts.

Another object of the present invention is to provide a method for preparing the peptide derivative or the pharmaceutically acceptable salt thereof.

Still another object of the present invention is to provide a cosmetic composition for improving wrinkles and inhibiting skin aging, including the peptide derivative or the pharmaceutically acceptable salt thereof.

Still another object of the present invention is to provide a pharmaceutical composition for improving wrinkles and inhibiting skin aging, including the peptide derivative or the pharmaceutically acceptable salt thereof.

Still another object of the present invention is to provide a method for improving skin wrinkles, including the step of applying the peptide derivative or the pharmaceutically acceptable salt thereof to the skin of an individual.

Still another object of the present invention is to provide a method for inhibiting skin aging, including the step of applying the peptide derivative or the pharmaceutically acceptable salt thereof to the skin of an individual.

Advantageous Effects

The biotin-conjugated hexapeptide-2 peptide derivative of the present invention has excellent effects of improving wrinkles and preventing skin aging, and effectively exhibits its intrinsic effects without side effects such skin irritation when applied to the human body, and thus is a very useful material in the industrial fields such as productions of medicines for external use and cosmetics. Further, the cosmetic and pharmaceutical compositions including the biotin-conjugated hexapeptide-2 peptide derivative of the present invention is worthy of notice as alternatives to the known methods and treatments for inhibiting skin aging by improving collagen biosynthesis in the skin.

BEST MODE

Figure 1:
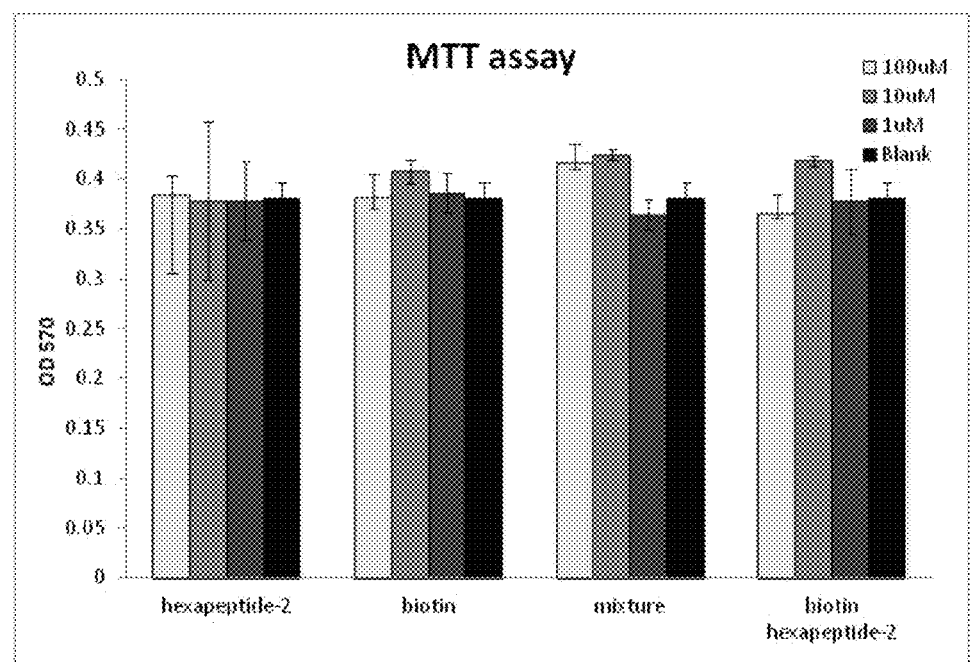
FIG. 1 shows the result of cytotoxicity assay of the biotin-conjugated hexapeptide-2 peptide derivative according to the present invention.

In one aspect to achieve the above objects, the present invention relates to a novel peptide derivative or a pharmaceutically acceptable salt thereof maximizing collagen synthetic ability of fibroblasts.

Specifically, the present invention relates to a peptide derivative having a structure of the following Chemical Formula 1 or a pharmaceutically acceptable salt thereof:

[Chemical Formula 1]

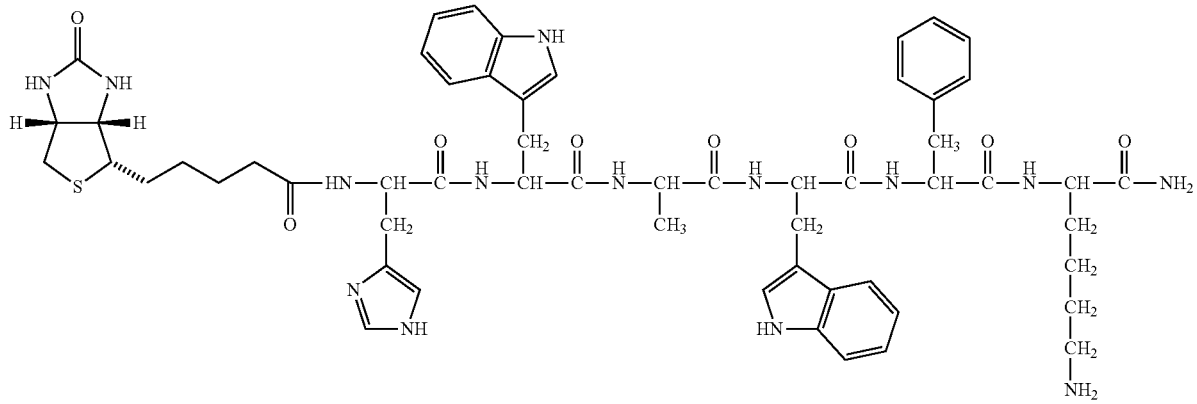

The peptide derivative of Chemical Formula 1 is a novel peptide derivative that is prepared by conjugation of biotin to hexapeptide-2 peptide (His-D-Trp-Ala-Trp-D-Phe-Lys-NH₂).

As used herein, the term 'pharmaceutically acceptable salt' includes salts that are derived from a pharmaceutically acceptable inorganic acid, organic acid or base. Examples of the suitable acid may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, trifluoroacetic acid, etc. Examples of the salts derived from suitable bases may include alkali metals such as sodium, etc., alkaline earth metals such as magnesium, etc., and ammonium, etc.

In another aspect, the present invention relates to a method for synthesizing the novel peptide derivative.

The peptide derivative of the present invention or the pharmaceutically acceptable salt thereof may be prepared by using a technique known in the art. The synthetic method is represented by the following description, but the present invention is not limited thereto, and the method can be appropriately modified by those skilled in the art within the scope of the technology known in the art.

In one specific embodiment of the present invention, the peptide derivatives having a moisturizing effect were prepared by standard solid phase peptide synthesis (SPPS) with Fmoc chemistry and solution chemistry.

The solid phase peptide synthetic method was performed according to total 6 steps of 1) loading protected amino acids onto a resin; 2) removing the protecting groups of amino acids; 3) inducing coupling reactions of amino acids; 4) monitoring the reactions (e.g., Kaiser test); 5) removing the resin and the protecting groups; and 6) solidifying the peptides.

Hereinafter, each step of the synthetic method will be described in more detail.

Step 1) is a step of loading amino acids and biotin onto a resin. The resin may include Wang resins, chlorotrityl resins, polystyrene resins or the like. For optimization of the synthesis, a resin of which reactive residues are bound with amine groups is used, and a suitable solvent is added to this amine resin to swell the resin. The solvent may be, for example, MC (methylene chloride), but is not limited thereto. Next, the solvent is removed under reduced pressure, and the protected amino acids dissolved in a suitable solvent and a mixture of DIC (diisopropylcarbodiimide) and DMAP (4-dimethylaminopyridine) were added to a vessel and reacted. The solvent may be, for example, DMF (dimethylformamide), and the protecting group of amino acid may be Fmoc (9-Fluorenylmethoxycarbonyl), but are not limited thereto.

Step 2 is a step of removing the protecting groups of amino acids. The removal of amino acid protecting groups may be performed according to a method generally known in the art. In the specific embodiment of the present invention, the amino acid solution loaded onto the resin was removed under reduced pressure, and the resin was washed, and then reacted with pipperidine in DMF solution to remove the protecting groups.

Step 3 is a step of inducing coupling reactions of amino acids. The amino acid coupling reaction may be performed according to a method generally known in the art, for example, HOBt-DCC (N-hydroxybenzotriazole-dicyclohexylcarodiimide) method or HOBt-DIC (N-hydroxybenzotriazole-diisopropylcarbodiimide) method (Wang C. Chan, Perter D. white, "Fmoc solid phase peptide synthesis", Oxford). In addition, coupling reagents such as N,N'-dicyclohexyl carbodiimide (DCC), N,N'-diisopropylcarbodiimide (DIC), O-benzotriazole-1-yl-N,N,N',N'-tetramethyluroniumhexafluorophosphate (HBTU), benzo-triazole-1-yl-oxytris(dimethylamino)phosphonium hexafluorophosphate (PyBOP), benzo-triazole-1-yl-oxytris(dimethylamino) phosphonium hexafluorophosphate (BOP), [O-(7-azabenzotri-azol-1-yl)-N,N,N',N'-tetramethyluroniumhexafluoro-phosphate] (HATU), 1H-hydroxy-benzotriazole (HOBt), 1H-hydroxy-7-azabenzotriazole (HOAt) or the like may be used to perform the synthesis, and an organic base such as trifluoroacetic acid (TFA), diisopropylethylamine (DIPEA), N-methylmorpholine (NMM) or the like may be added depending on the coupling reagent to perform the reaction, but is not limited thereto.

Step 4 is a step of monitoring the reaction. In the specific embodiment of the present invention, for example, the Kaiser test (E. Kaiser et al., Anal. Biochem. (1970) 34, 595) was used in order to monitor the coupling reaction of amino acids. The Kaiser test is a qualitative method of detecting the presence of primary amine functional groups by color changes using ninhydrin. In detail, after amino acid coupling reactions, 2-3 drops of a Kaiser test solution are added to a small amount of the washed resin, and then color changes of the resin are observed for a predetermined time. No color change of the resin indicates that the coupling reaction is successful, and thus the next reaction is proceeded. A blue color of the resin indicates the presence of unreacted amino acids, and thus the amino acid coupling reactions should be repeated.

Step 5 is a step of removing the resin and the protecting groups. The peptides synthesized by repeating Step 3 to 5 are removed from the resin, and the protecting groups of the amino acid side chains are deprotected. The removal of the resin and the amino acid protecting group may be performed according to a method generally known in the art. In the specific embodiment of the present invention, a cleavage cocktail solution consisting of TFA (trifluoroacetic acid), TIS (triisopropylsilane), thioanisole, $H_2O$, and EDT (ethanedithiol) was added to obtain a peptide solution. The constitution of the solution may be appropriately modified by those skilled in the art, depending on experimental conditions.

Step 6 is a step of solidifying the peptides. For example, an excessive amount of diethyl ether solvent may be added to produce solid precipitation, but is not limited thereto.

The peptide derivative according to the present invention and the pharmaceutically acceptable salt thereof showed no side effect such as cytotoxicity on the skin fibroblasts (FIG. 1), and showed a strong ability to promote collagen biosynthesis in the skin fibroblasts. In particular, single or combination treatment of hexapeptide-2 and biotin showed no increase in type 1 collagen biosynthesis, but the biotin-conjugated hexapeptide-2 showed a significant increase in type 1 collagen biosynthesis (FIG. 2).

In still another aspect, the present invention relates to a composition for improving wrinkles and preventing skin aging, including the peptide derivative of the present invention or the pharmaceutically acceptable salt thereof. The composition for improving wrinkles and preventing skin aging including the peptide derivative of the present invention or the pharmaceutically acceptable salt thereof as an active ingredient encompasses both cosmetic and pharmaceutical compositions according to the use and the desired effects.

In the preferred embodiment, the present invention relates to cosmetic and pharmaceutical compositions for improving wrinkles and inhibiting skin aging, including the peptide derivative of the present invention or the pharmaceutically acceptable salt thereof.

In still another aspect, the present invention relates to a method for improving skin wrinkles, including the step of applying the peptide derivative of the present invention or the pharmaceutically acceptable salt thereof to the skin of an individual.

In still another aspect, the present invention relates to a method for inhibiting skin aging, including the step of applying the peptide derivative of the present invention or the pharmaceutically acceptable salt thereof to the skin of an individual.

When it is used as the cosmetic and pharmaceutical compositions for improving wrinkles and inhibiting skin aging, the composition may be applied to the skin, scalp or hair, and may be used in order to prevent skin aging, and improve wrinkles and rough skin.

The content of the peptide derivative in the composition for improving wrinkles and inhibiting skin aging of the present invention may be properly controlled according to use of the composition, application type, purpose of use and desired effects, and is preferably 0.0001 to 99% by weight, preferably 0.001 to 50% by weight, more preferably 0.001 to 1% by weight, and most preferably 0.005 to 0.1% by weight, based on the total weight of the composition, in view of cost versus effect.

The composition for improving wrinkles and preventing skin aging of the present invention may be administered via oral or parenteral routes, for example, via oral, percutaneous, subcutaneous, or intravenous routes, preferably via a percutaneous route for parenteral administration, and more preferably via topical application.

The composition may be percutaneously applied to the skin, scalp or hair, and it means a composition that can be used in the production of all cosmetic products such as fundamental cosmetics, creams for bust and hip, make-up products, body care products, shaving products, hair care products, etc. The composition may be formulated in the form of an ointment, spray, suspension, emulsion, cream, gel, foam, etc., but there is no particular limitation in its formulation.

Preferably, the cosmetic composition may have a formulation selected from the group consisting of skin softener, astringent lotion, nutrient lotion, nutrient cream, massage cream, eye cream, eye essence, essence, cleansing cream, cleansing lotion, cleansing foam, cleansing water, pack, powder, body lotion, body cream, body essence, body wash, sunscreen cream, hair dye, shampoo, rinse, toothpaste, oral refresher, hair conditioner, hair tonic, lotion, ointment, gel, cream, patch and spray.

The cosmetic and pharmaceutical compositions of the present invention may further include all kinds of ingredients that can be used in the typical production or formulation, for example, a fragrance, a coloring agent, a bactericidal agent, an antioxidant, a preservative, a moisturizer, a thickening agent, an excipient, a diluent, a mineral, a synthetic polymer, etc., in addition to the above effective ingredients, and the type and content can be properly adjusted according to use of the final product and purpose of use.

The composition of the present invention may further include a solvent that can be typically included in the formulation, for example, one or more selected from ethanol, glycerin, butylene glycol, propylene glycol, polyethylene glycol, 1,2,4-butanetriol, sorbitol ester, 1,2,6-hexanetriol, benzyl alcohol, isopropanol, butanediol, diethylene glycol monoethyl ether, dimethyl isosorbide, N-methyl-2-pyrrolidone, propylene carbonate, glycereth-26, methylgluces-20, isocetylmyristate, isocetyloctanoate, octyldodecyl myristate, octyldodecanol, isostearyl isostearate, cetyl octanoate, and neopentyl glycol dicaprate. When the composition of the present invention is prepared using these solvents, the solubility of the compound to the solvent varies slightly, depending on the particular compound and the mixing ratio of the solvents. However, those skilled in the art can select the particular solvent and its content adequately, depending on the characteristics of the product.

Further, the composition of the present invention may include various materials for enhancing percutaneous penetration upon percutaneous administration, for example, laurocapram derivatives, oleic acid, ester derivatives of monooleate derivative, adapalene, tretinoin, retinaldehyde, tazarotene, salicylic acid, azelaic acid, glycolic acid, ethoxydiglycol, Tween 80, lecithin organogel, etc. In order to provide additional functions, the composition of the present invention may further include other ingredients such as a cosurfactant, a surfactant, an anti-dandruff agent, a callus softener, a blood flow stimulant, a cell activator, a refreshing agent, a moisturizing agent, an antioxidant, a pH adjuster, purified water, etc., within the scope of not affecting the moisturizing effect of the composition. The composition may also include a proper additive such as a fragrance, a color, a preservative, an excipient, etc., depending on the applied form.

MODE FOR INVENTION

Hereinafter, the present invention will be described in detail with reference to Examples. However, these examples are for illustrative purposes only, and the present invention is not intended to be limited by the following Examples.

Example 1

Preparation of Peptide Derivative

In the present invention, peptide derivatives were prepared by standard solid phase peptide synthesis using Fmoc(9-luorenylmethoxycarbonyl) as a Nα-amino acid protecting group, and specific example thereof is as follows.

First, the amount of Amine resin (1.1 mmol/g, Novabiochem Corporation) corresponding to 1 mmol was weighed and put in a reaction vessel, and then 30 ml of MC was added to swell the resin for 10 minutes. The solvent was removed under reduced pressure, and Fmoc-lysine (4 eq.) in DMF solvent, and a mixture of DIC (2 eq.; Diisopropylcarbodiimide) & DMAP (0.1 eq.; 4-Dimethylaminopyridine) were added to the vessel and reacted for 4 hours. Next, the amino acid solution loaded to the Amine resin was removed under reduced pressure, and the resin was washed with each 30 ml of DMF and MC 5 times. The Fmoc-lysine-loaded resin was reacted with 20% (v/v %) pipperidine in DMF solution for 10 minutes for deprotection, and then washed with each 30 ml of DMF and MC 5 times. Next, Fmoc peptides and biotin dissolved in DMF solvent (use Fmoc-D-phenylalanine, Fmoc-tryptophan, Fmoc-alanine, Fmoc-D-tryptophan, Fmoc-histidine, and biotin in this order) (each 4 eq.), DIC (4 eq.; Diisopropylcarbodiimide) and HOBt (4 eq.; N-hydroxybenzotriazole) as a coupling reagent were added to the Fmoc-deprotected resin, and reacted at room temperature for 4 hours to induce amino acid coupling reactions. After amino acid coupling reactions, 2-3 drops of Kaiser test solution A, B, C [solution A: ninhydrin (5 g) in ethanol (100 ml), solution B: phenol (80 g) in ethanol (20 ml), solution C: 0.1 M KCN (2 ml) in pyridine (98 ml)] were added to a small amount of the washed resin, and maintained at 100° C. to observe color changes of the resin for 10 minutes. No color change of the resin indicates that the coupling reaction is successful, and thus the next reaction was proceeded. A blue color of the resin indicates the presence of unreacted amino acids, and thus the amino acid coupling reactions should be repeated.

The peptides synthesized by the above procedures were removed from the resin. In order to deprotect the protecting groups of the amino acid side chains, a mixture consisting of TFA (trifluoroacetic acid), TIS (triisopropylsilane), thioanisole, $H_2O$, and EDT (ethanedithiol) was added at a ratio of 90:2.5:2.5:2.5:2.5 to produce solid precipitation. The resulting precipitates were centrifuged to remove the remaining TFA, TIS, thioanisole, $H_2O$, and EDT, and this procedure was repeated three or more times so as to obtain solid biotin-conjugated hexapeptide-2 peptides.

For analysis of the biotin-conjugated hexapeptide-2 peptide, RP-HPLC and LC-MS were performed.

In RP-HPLC, buffer A was 0.1% TFA-containing water, and buffer B was 0.1% TFA-containing acetonitrile, and analysis was performed with a concentration gradient from 5% to 65% buffer B for 30 minutes. As a result, Rt was approximately 25.808 minutes.

In LC-MS, the predicted value was 1099.3 Da, and the experimental value was 1099.1 Da.

Example 2

Cytotoxicity Test of Biotin-Conjugated Hexapeptide-2 Peptide Derivative

In order to examine cytotoxicity of the biotin-conjugated hexapeptide-2 peptide synthesized in Example 1, the following experiment was performed. Cytotoxicity was examined by MTT assay, and a control group with no sample added was considered as 100% to calculate relative cytotoxicity. The detailed experimental method is as follows.

Human normal fibroblasts (Human Dermal Fibroblast neonatal) were seeded in a 96-well plate for cell culture at a density of 3,000 cells per well, and cultured in 10% FBS (Fetal bovine serum)-containing DMEM (Dulbecco's Modified Eagle Media, Gibco BRL) in a 37° C., 5% $CO_2$ incubator for 24 hours. Each test material was dissolved in water at a concentration of 10 mM to prepare concentrates, and the concentrates were diluted with 0.5% FBS-containing DMEM at a concentration of 200 uM, 20 uM, and 2 uM. Then, each 100 ul of the diluted solutions was added to each well previously containing 100 ul of the medium, followed by incubation for 48 hours. After completing the cultivation, the supernatants were used to determine the amount of type 1 collagen produced (Example 3), and the cells were used to determine cytotoxicity.

In MTT assay for determining cytotoxicity, 90 ul of 10% FBS-containing DMEM was added to each of the culture medium-removed wells, and 10 ul of 3-(4,5-dimethylthiazol-2-yl)-2,5-diphenyltetrazolium bromide (MTT) dissolved in PBS at a concentration of 5 mg/ml was added, followed by incubation under the conditions of 37° C. and 5% $CO_2$ for 3 hours. Thereafter, the supernatant was carefully removed, and MTT formazan precipitates in the cells were dissolved in 100 ul of DMSO to determine absorbance at OD570 using an ELISA reader.

Figure 2:
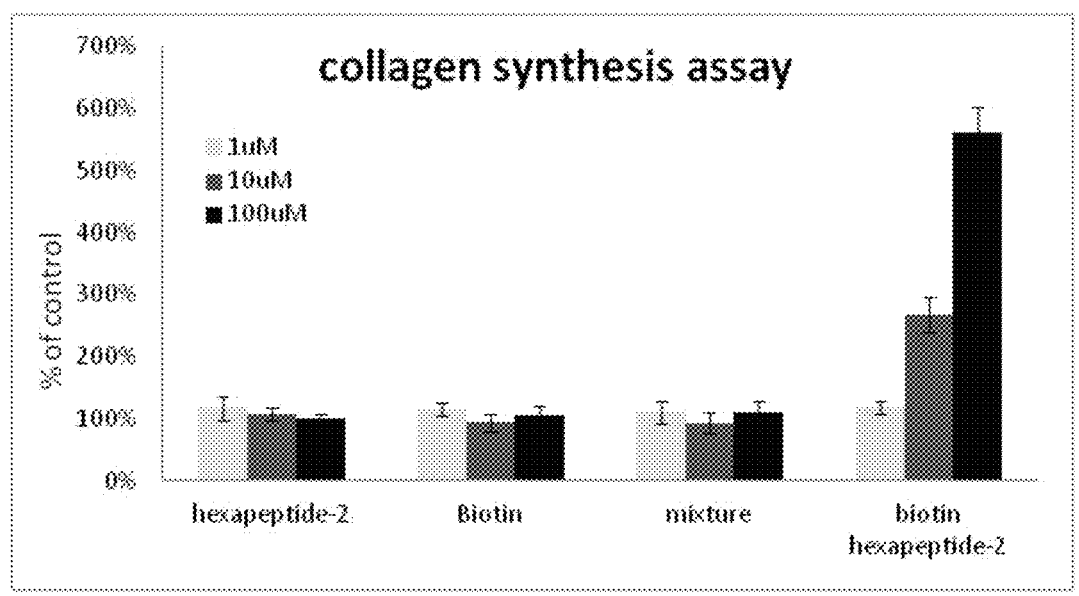
FIG. 2 shows the result of collagen biosynthesis assay of the biotin-conjugated hexapeptide-2 peptide derivative according to the present invention.

The results are shown in FIG. 1. As shown in FIG. 1, the biotin-conjugated hexapeptide-2 of the present invention showed no cytotoxicity, as in single or combination treatment of hexapeptide-2 and biotin.

Example 3

Measurement of Type 1 Collagen Biosynthesis-Promoting Ability of Biotin-Conjugated Hexapeptide-2 Peptide Derivative In order to examine type 1 collagen biosynthesis-promoting ability of the biotin-conjugated hexapeptide-2 peptide synthesized in Example 1, the following experiment was performed. The type 1 collagen produced was measured by ELISA assay to examine the effect of promoting collagen biosynthesis, and a control group with no sample added was considered as 100% to calculate the relative type 1 collagen production ability. The detailed experimental method is as follows.

First, a 96-well plate was coated with antibodies against type 1 collagen, and fully blocked using a blocking buffer. Thereafter, fibroblast culture supernatants described in Example 2 were treated to the 96-well plate coated with type 1 collagen antibodies, and reacted at room temperature for 2 hours. After completing the reaction, the supernatants were removed, and the plate was washed with 0.05% Tween 20-containing PBS (PBST), and biotin-conjugated secondary antibodies were treated to the 96-well plate, followed by incubation at room temperature for 1 hour. After completing the reaction, the remaining supernatants were removed in the same manner as above. After washing with PBST, SA-HRP (streptavidin-horseradish peroxidase, Sigma) was bound to measure the bound collagen. After treating with TMB (3,3'-5,5' tetramethylbenzidine, Sigma) as a substrate for color development, reaction was performed at room temperature for 15 minutes, while blocking light. Reaction was stopped using 2 N hydrochloric acid, and absorbance was measured at 450 nm. For comparison of the effects, type 1 collagen biosynthesis was measured in single treatment of hexapeptide-2, single treatment of biotin, and combination treatment of a mixture of hexapeptide-2 and biotin.

The results are shown in FIG. 2. As shown in FIG. 2, single or combination treatment of hexapeptide-2 and biotin showed no increase in type 1 collagen biosynthesis, but the biotin-conjugated hexapeptide-2 showed a significant increase in type 1 collagen biosynthesis.

The invention claimed is:

1. A peptide derivative having a structure of the following Chemical Formula 1 or a pharmaceutically acceptable salt thereof:

[Chemical Formula 1]

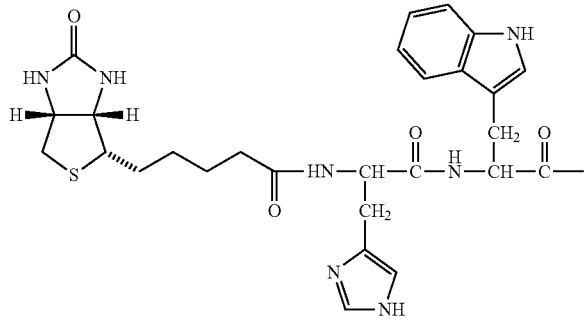

-continued

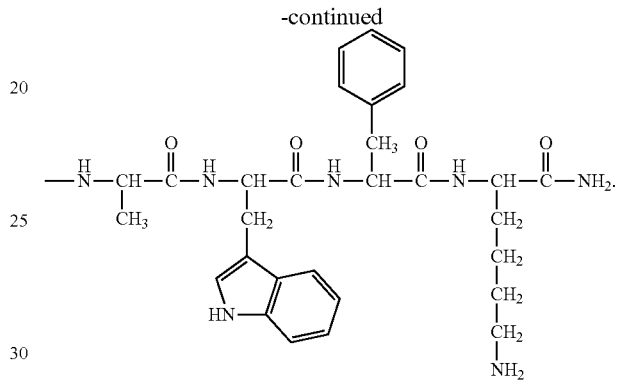

2. A cosmetic composition for improving wrinkles and preventing skin aging, comprising the peptide derivative or the pharmaceutically acceptable salt thereof of claim 1.

3. The cosmetic composition according to claim 2, wherein the cosmetic composition has a formulation selected from the group consisting of skin softener, astringent lotion, nutrient lotion, nutrient cream, massage cream, eye cream, cleansing cream, cleansing lotion, cleansing foam, cleansing water, powder, body lotion, body cream, body wash, sunscreen cream, hair dye, shampoo, rinse, toothpaste, oral refresher, hair conditioner, hair tonic, lotion, ointment, gel, cream, patch and spray.

4. A pharmaceutical composition for improving wrinkles and preventing skin aging, comprising the peptide derivative or the pharmaceutically acceptable salt thereof of claim 1.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: KTTKS peptide

<400> SEQUENCE: 1

Lys Thr Thr Lys Ser
 1               5